US012662709B2

(12) United States Patent
Qi et al.

(10) Patent No.: US 12,662,709 B2
(45) Date of Patent: Jun. 23, 2026

(54) RT-PCR DETECTION REAGENT FOR DETECTING NOVEL CORONAVIRUS, KIT AND DETECTION METHOD THEREOF

(71) Applicant: SHANGHAI FOCUSGEN BIOTECH LTD, Shanghai (CN)

(72) Inventors: Lifeng Qi, Shanghai (CN); Yong Yan, Jiaxing City (CN)

(73) Assignee: SHANGHAI FOCUSGEN BIOTECH LTD, Shanghai (CN)

( * ) Notice: Subject to any disclaimer, the term of this patent is extended or adjusted under 35 U.S.C. 154(b) by 0 days.

(21) Appl. No.: 17/594,489

(22) PCT Filed: Jun. 8, 2021

(86) PCT No.: PCT/CN2021/098830
§ 371 (c)(1),
(2) Date: Oct. 19, 2021

(87) PCT Pub. No.: WO2022/257002
PCT Pub. Date: Dec. 15, 2022

(65) Prior Publication Data

US 2023/0203603 A1 Jun. 29, 2023

(51) Int. Cl.
*C12Q 1/68* (2018.01)
*C12Q 1/686* (2018.01)
*C12Q 1/70* (2006.01)

(52) U.S. Cl.
CPC ............. *C12Q 1/701* (2013.01); *C12Q 1/686* (2013.01); *C12Q 2600/16* (2013.01)

(58) Field of Classification Search
CPC .................................... C12Q 1/70; C12Q 1/68
See application file for complete search history.

(56) References Cited

U.S. PATENT DOCUMENTS

| | | | | |
|---|---|---|---|---|
| 2003/0050470 A1* | 3/2003 | An | C07H 21/00 | 435/6.14 |
| 2004/0023207 A1* | 2/2004 | Polansky | A61K 48/005 | 435/456 |

FOREIGN PATENT DOCUMENTS

| | | | | |
|---|---|---|---|---|
| CN | 110982943 A | | 4/2020 | |
| CN | 111020064 A | | 4/2020 | |
| CN | 111270013 A | * | 6/2020 | C12Q 1/6851 |
| WO | WO-2006121773 A2 | * | 11/2006 | C12Q 1/6883 |
| WO | WO-2007095155 A2 | * | 8/2007 | C12Q 1/701 |
| WO | WO-2008042450 A2 | * | 4/2008 | C12Q 1/701 |
| WO | WO-2021231968 A1 | * | 11/2021 | C12Q 1/686 |
| WO | WO-2022257002 A1 | * | 12/2022 | |

OTHER PUBLICATIONS

Chung et al., 2021. Novel dual multiplex real-time RT-PCR assays for the rapid detection of SARS-CoV-2, influenza A/B, and respiratory syncytial virus using the BD MAX open system. Emerging microbes & infections, 10(1), pp. 161-166. (Year: 2021).*

Corman et al., 2020. Detection of 2019 novel coronavirus (2019-nCoV) by real-time RT-PCR. Eurosurveillance, 25(3), 2000045, pp. 23-30. (Year: 2020).*

English Translation of CN111270013A, publ. Jun. 2020. (Year: 2020).*

Gadberry MD, Malcomber ST, Doust AN, Kellogg EA. Primaclade—a flexible tool to find conserved PCR primers across multiple species. Bioinformatics. Apr. 1, 2005;21(7):1263-4. (Year: 2005).*

Gao et al., 2011. Development of the real-time RT-PCR detection system for determination of pandemic influenza A (H1N1) virus. Acta virologica, 55(1), p. 85. (Year: 2011).*

Genbank Accession No. NM_001101.4—*Homo sapiens* actin beta (ACTB), mRNA (submitted Oct. 2018, retrieved on Sep. 5, 2023 from http://www.ncbi.nlm.nih.gov/nuccore/NM_001101). (Year: 2018).*

Genbank Accession No. FJ969513—Influenza A virus (A/California/04/2009(H1N1)) segment 7 matrix protein 2 (M2) and matrix protein 1 (M1) genes, complete cds. submitted Apr. 28, 2009, retrieved on Sep. 3, 2023 from http://www.ncbi.nlm.nih.gov/nuccore/FJ969513). (Year: 2009).*

Genbank Accession No. FJ969537—Influenza A virus (A/California/07/2009(H1N1)) segment 7 matrix protein 2 (M2) and matrix protein 1 (M1) genes, complete cds (submitted Apr. 28, 2009, retrieved on Sep. 5, 2023 from http://www.ncbi.nlm.nih.gov/nuccore/FJ969537). (Year: 2009).*

Genbank Accession No. KP317439—Influenza A virus (A/Delhi/053/2011(H1N1)) segment 7 matrix protein 2 (M2) gene, partial cds; and matrix protein 1 (M1) gene, complete cds (submitted Dec. 24, 2014, retrieved on Sep. 3, 2023 from http://www.ncbi.nlm.nih.gov/nuccore/KP317439). (Year: 2014).*

Genbank Accession No. JX414012—Influenza A virus (A/reassortant/IVR-148(Brisbane/59/2007 x Texas/1/1977)(H1N1)) segment 7 matrix protein 2 (M2) and matrix protein 1 (M1) genes, complete cds (submitted Jul. 20, 2012, retrieved on Sep. 5, 2023 from http://www.ncbi.nlm.nih.gov/nuccore/JX414012). (Year: 2012).*

Genbank Accession No. CY093580—Influenza B virus (B/Singapore/1/2011) nucleoprotein (NP) gene,complete cds (submitted Jul. 21, 2011, retrieved on Sep. 5, 2023 from http://www.ncbi.nlm.nih.gov/nuccore/CY093580). (Year: 2011).*

Genbank Accession No. KT223814—Influenza B virus (B/California/NHRC_M1023/2014) segment 8 nuclear export protein (NEP) gene, partial cds; and nonstructural protein 1(NS1) gene, complete cds (submitted Jul. 1, 2015, retrieved on Sep. 3, 2023 from http://www.ncbi.nlm.nih.gov/nuccore/KT223814). (Year: 2015).*

(Continued)

*Primary Examiner* — Gary Benzion
*Assistant Examiner* — Olayinka A Oyeyemi
(74) *Attorney, Agent, or Firm* — HAUPTMAN HAM, LLP

(57) ABSTRACT

The present application relates to the molecular biological detection technical field, specifically is a RT-PCR detection reagent for detecting coronavirus virus directly without need of RNA extraction, a kit and a detection method thereof. The RT-PCR detection reagent for detecting coronavirus virus comprises primers having nucleotide sequences as set forth in SEQ ID NO. 1-2, 3-4, and 13-14.

5 Claims, 1 Drawing Sheet

Specification includes a Sequence Listing.

(56) References Cited

OTHER PUBLICATIONS

Genbank Accession No. CY232070—Influenza B virus (B/Colorado/06/2017) nuclear export protein (NEP)and nonstructural protein 1 (NS1) genes, complete cds (submitted May 17, 2017, retrieved on Sep. 5, 2023 from http://www.ncbi.nlm.nih.gov/nuccore/CY232070). (Year: 2017).*
Genbank Accession No. MT072688—Severe acute respiratory syndrome coronavirus 2 isolate SARS-CoV-2/human/NPL/61-TW/2020, complete genome (submitted Feb. 16, 2020, retrieved on Sep. 4, 2023 from http://www.ncbi.nlm.nih.gov/nuccore/MT072688). (Year: 2020).*
Genbank Accession No. MN908947—Severe acute respiratory syndrome coronavirus 2 isolate Wuhan-Hu-1, complete genome (submitted Jan. 5, 2020, retrieved on Sep. 5, 2023 from http://www.ncbi.nlm.nih.gov/nuccore/MN908947). (Year: 2020).*
Genbank Accession No. NC_045512—Severe acute respiratory syndrome coronavirus 2 isolate Wuhan-Hu-1, complete genome (submitted Jan. 2020, retrieved on Sep. 5, 2023 from http://www.ncbi.nlm.nih.gov/nuccore/NC_045512). (Year: 2020).*
Lee et al., 2012. A universal influenza A and B duplex real-time RT-PCR assay. Journal of medical virology, 84(10), pp. 1646-1651. (Year: 2012).*
Lu et al., Aug. 2020. US CDC real-time reverse transcription PCR panel for detection of severe acute respiratory syndrome coronavirus 2. Emerging infectious diseases, 26(8), p. 1654-1665. (Year: 2020).*
National Health Commission of the People's Republic of China, Mar. 1, 2020, Technical guidance for laboratory testing of 2019-nCoV infection (Third Edition), Biosafety and Health, 2(01) , pp. 3-5, (Year: 2020).*
SantaLucia Jr, John. Physical principles and visual-OMP software for optimal PCR design. PCR Primer Design. Humana Press, 2007: pp. 3-33. (Year: 2007).*
Selvaraju et al., 2010. Evaluation of three influenza A and B real-time reverse transcription-PCR assays and a new 2009 H1N1 assay for detection of influenza viruses. Journal of clinical microbiology, 48(11), pp. 3870-3875. (Year: 2010).*
Shu et al., 2021. Multiplex real-time reverse transcription PCR for influenza A virus, influenza B virus, and severe acute respiratory syndrome coronavirus 2. Emerging infectious diseases, 27(7), p. 1821-1830. (Year: 2021).*
Van Elden et al., 2001. Simultaneous detection of influenza viruses A and B using real-time quantitative PCR. Journal of clinical microbiology, 39(1), pp. 196-200. (Year: 2001).*
Vogels et al., 2020. Analytical sensitivity and efficiency comparisons of SARS-CoV-2 RT-qPCR primer-probe sets. Nature microbiology, 5(10), pp. 1299-1305. (Year: 2020).*
Yan et al., 2017. A multiplex liquid-chip assay based on Luminex xMAP technology for simultaneous detection of six common respiratory viruses. Oncotarget, 8(57), pp. 96913-96923. (Year: 2017).*
Zhang et al., 2019. Development of a multiplex real-time RT-PCR assay for simultaneous detection and differentiation of influenza A, B, C, and D viruses. Diagnostic microbiology and infectious disease, 95(1), pp. 59-66. (Year: 2019).*
Zhang et al., 2010. Direct DNA amplification from crude clinical samples using a PCR enhancer cocktail and novel mutants of Taq. The Journal of Molecular Diagnostics, 12(2), pp. 152-161. (Year: 2010).*
Genbank Accession No. MT276598—Severe acute respiratory syndrome coronavirus 2 isolate SARS-CoV-2/human/ISR/ISR_IT0320/2020. submitted Apr. 2, 2020, retrieved from http://www.ncbi.nlm.nih.gov/nuccore/MT2756598). (Year: 2020).*
Ji et al., 2020. Automated multiplex nucleic acid tests for rapid detection of SARS-CoV-2, influenza A and B infection with direct reverse-transcription quantitative PCR (dirRT-qPCR) assay in a centrifugal microfluidic platform. RSC advances, 10(56), pp. 34088 (Year: 2020).*
International Search Report and Written Opinion issued in International Application No. PCT/CN2021/098830; mailed Mar. 16, 2022; 11 pgs.
Huang, Wei E. et al; RT-LAMP for rapid diagnosis of coronavirus SARS-CoV-2; Microbial Biotechnology, Apr. 25, 2020; No. 4 vol. 13; 950-961pgs.
Wang, Huihui et al.; The genetic sequence, origin, and diagnosis of SARS-CoV-2; European Journal of Clinical Microbiology & Infectious Disease, Apr. 24, 2020; No. 9 vol. 39; pp. 1629-1635.

* cited by examiner

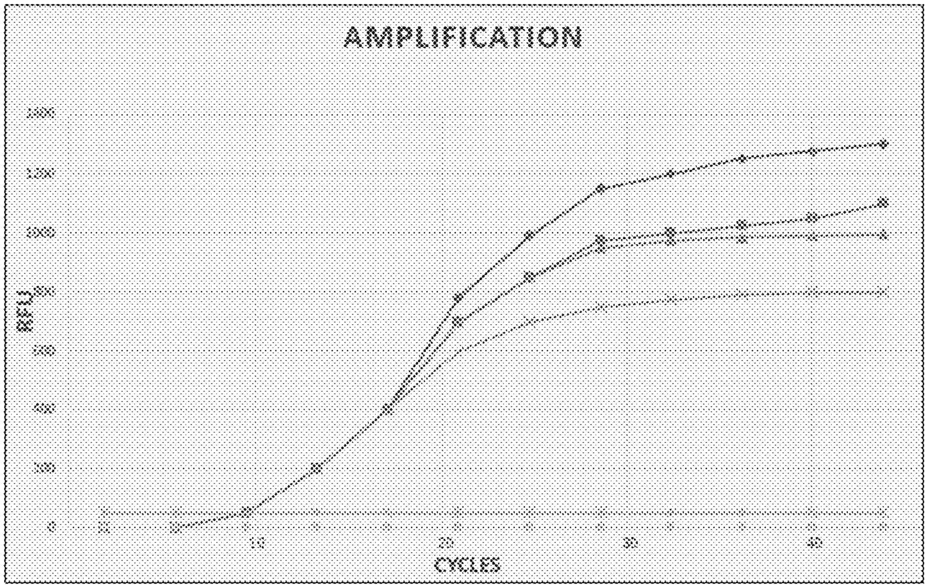
AMPLIFICATION
RFU
0
10
20
30
40
CYCLES

RT-PCR DETECTION REAGENT FOR DETECTING NOVEL CORONAVIRUS, KIT AND DETECTION METHOD THEREOF

TECHNICAL FIELD

The present application relates to the molecular biological detection technical field, specifically is a RT-PCR detection reagent for detecting coronavirus, a kit and a detection method thereof.

BACKGROUND

Coronaviruses are a large family of viruses which may cause illness in animals or humans. In humans, several coronaviruses are known to cause respiratory infections ranging from the common cold to more severe diseases such as Middle East Respiratory Syndrome (MERS) and Severe Acute Respiratory Syndrome (SARS). The most recently discovered coronavirus causes coronavirus disease COVID-19.

The novel coronaviruses belong to the β genus. COVID-19 is an acute respiratory infectious disease to which humans are generally susceptible. Currently, the patients infected by the novel coronavirus are the main source of infection, though asymptomatic infected people can also be an infectious source. Based on the current epidemiological investigation, the incubation period tends to be 3 to 7 days but can be anytime from 1 to 14 days. The main manifestations of the virus include fever, fatigue, and dry cough. Nasal congestion, runny nose, sore throat, myalgia, and diarrhea may also occur. Influenza virus (IFV) A (a) and B (b) are the most common respiratory viruses in winter and spring. Detection of influenza virus and Severe Acute Respiratory Syndrome Coronavirus 2 (SARS-CoV-2) nucleic acid in cases of viral pneumonia is conducive to the etiological diagnosis of viral pneumonia.

The global epidemic prevention situation of the novel coronavirus is still severe. The total number of confirmed diagnoses worldwide has exceeded 20 million. There are 6 million confirmed diagnoses and an average of 230,000 confirmed daily. At present, there are still a large number of asymptomatic or mildly infected people, the length of the incubation period of infection is different, the missed detection and the sensitivity of reagent stability are not consistent, the lack of effective detecting reagents causes the large inventory of testing, and the heavy work of the testing personnel, etc., urgently need to focus on development Emergency rapid nucleic acid detection equipment and supporting reagents, which are fast, portable, reliable and easy to use, in order to effective control of the current epidemic.

The coronavirus detection methods mainly include nucleic acid detection, antibody detection, and antigen detection. Due to the low detection rate of antigen testing, the current coronavirus testing mainly focuses on antibody and nucleic acid testing. Nucleic acid detection is currently the "gold standard" for the detection of new coronaviruses. Nucleic acid detection has the characteristics of early diagnosis, high sensitivity and specificity; but antibody detection is convenient and rapid, and can be used as a supplementary method for nucleic acid diagnosis.

By now, the China Food and Drug Administration has approved nucleic acid detection reagents and antibody detection reagents. Among them, antibody detection reagents include colloidal gold methods and magnetic microparticle chemiluminescence methods. With the progress of understanding of diseases and research and development, more detection reagents and methods will be put into use in the future.

The first type of nucleic acid detection method includes multiple steps such as specimen processing, nucleic acid extraction, and PCR detection. The average detection time takes 2-3 hours. Because the first type of nucleic acid detection directly detects the viral nucleic acid in the specimens collected, the nucleic acid detection has strong specificity and relatively high sensitivity, and is currently the main detection method. The second type of antibody detection includes colloidal gold method and magnetic microparticle chemiluminescence method. The average detection time of colloidal gold method is about 15 minutes. A drop of blood can be detected with the naked eye within 15 minutes, this is the colloidal gold method, but if serum is used instead of whole blood, this serum treatment will take a while, and if whole blood is used, the colloidal gold method will take about 15 minutes. Magnetic microparticle chemiluminescence method generally takes 30-60 minutes. Antibody detection is to detect the level of antibodies in human blood. In the early stage of infection of the disease, the human body may not produce antibodies, so there is a detection window. Therefore, antibody detection can be used to assist in the diagnosis of cases with negative nucleic acid testing, and can also be used to screen cases, but antibody detection method cannot replace nucleic acid detection methods.

The clinical diagnosis of novel coronavirus urgently needs to provide nucleic acid detection reagents with high sensitivity, rapid and high-throughput detection in order to adapt to the effective control of the current novel coronavirus pneumonia epidemic in the world. In the early stage of the epidemic, the Medical Device Registration Management Department of the National Medical Products Administration approved more than 20 novel coronavirus nucleic acid detection reagent products through the emergency approval channel, but the currently approved nucleic acid detection kits all use two-step detection technology, which includes nucleic acid extraction. Using the two steps of PCR amplification, a detection with a single and closed tube cannot be achieved, so there is a risk of aerosol contamination. In addition, clinical results proved that a certain proportion of patients, especially asymptomatic or mildly symptomatic patients, has false negatives. In addition to errors of patient sample collection, the sensitivity of the detection kit is also a factor.

SUMMARY

Accordingly, at least one object of the present application is to provide a RT-PCR detection reagent for detecting coronavirus, a kit and a detection method thereof.

The kit of the present application uses a highly tolerable enzyme, adding activator, which can simultaneously release and detect nucleic acid, leading to "closed tube" detection of target genes, especially suitable for on-site rapid diagnosis and detection. In the kit of the present application, the specific genes of A (a) and B (b) influenza virus (IFV) and SARS-CoV-2 virus and the housekeeping genes of human were detected simultaneously by multiple real-time RT-PCR based on fluorescence probe analysis. Human housekeeping gene is used as an internal reference (IC) to monitor sampling quality. At the same time, uracil-DNA glycosylase (UDG) enzyme antifouling scheme is used in the kit of the present application to prevent the pollution of nucleic acid.

The kit of the present application is usable for the on-site rapid diagnosis and screening of the SARS-CoV-2 pneumonia by the multiple direct RT-PCR method without RNA extraction. The nucleic acid detection of SARS-CoV-2 occurred in the open reading frame ORFab and the nucleocapsid protein N gene.

One non-limited embodiment of the application provides a RT-PCR detection reagent for detecting coronavirus, comprising:

primer sequences of a SARS-CoV-2 ORF1lab gene as following:

a upstream primer has the nucleotide sequence of SEQ ID NO. 1; and a downstream primer has the nucleotide sequence of SEQ ID NO. 2; and primer sequences of a SARS-CoV-2 N gene fragment as following:

a upstream primer has the nucleotide sequence of SEQ ID NO. 3; and a downstream primer has the nucleotide sequence of SEQ ID NO. 4.

The RT-PCR detection reagent according to the present application, further comprising: primer sequences of an influenza A (IFV-A) gene as following:

a upstream primer has the nucleotide sequence of SEQ ID NO. 5; and a downstream primer has the nucleotide sequence of SEQ ID NO. 6; and primer sequences of an influenza B (IFV-B) gene as following:

a upstream primer has the nucleotide sequence of SEQ ID NO. 7; and a downstream primer has the nucleotide sequence of SEQ ID NO. 8.

The RT-PCR detection reagent according to the present application, further comprising:

a fluorescent probe sequence of an influenza A (IFV-A) gene having the nucleotide sequence of SEQ ID NO. 9;

a fluorescent probe sequence of an influenza B (IFV-B) gene having the nucleotide sequence of SEQ ID NO. 10;

a fluorescent probe sequence of a SARS-CoV-2 ORF1lab gene having the nucleotide sequence of SEQ ID NO. 11; and a fluorescent probe sequence of a SARS-CoV-2 N gene fragment having the nucleotide sequence of SEQ ID NO. 12.

The RT-PCR detection reagent according to the present application, further comprising primer and fluorescent probe sequences of an internal reference gene as following:

a upstream primer has the nucleotide sequence of SEQ ID NO. 13; and a downstream primer has the nucleotide sequence of SEQ ID NO. 14.

The RT-PCR detection reagent according to the present application, further comprising a fluorescent probe sequence of an internal reference gene having the nucleotide sequence of SEQ ID NO. 15.

The RT-PCR detection reagent according to the present application, wherein the coronavirus SARS-CoV-2.

The RT-PCR detection reagent according to the present application, further comprising following fluorescent probes:

IFV A-probe: FAM-SEQ ID NO. 16-BHQ1;

IFV B-probe: HEX-SEQ ID NO. 17-BHQ1;

SAS-CoV-2-probe: ROX-SEQ ID NO. 18-BHQ2, and ROX-SEQ ID NO. 19-BHQ2, and

IC-probe: Cy5-SEQ ID NO. 20-BHQ2.

One non-limited embodiment of the application provides a RT-PCR detection kit comprising the RT-PCR detection reagent according to the present application.

The RT-PCR detection kit according to the present application, wherein the kit further comprises one or more of sterile water, dNTP, PCR buffer, Hot Start Taq enzyme. The RT-PCR detection kit according to the present application, wherein the kit further comprises one or more of sterile water, dNTP, PCR buffer, Hot Start Taq enzyme, PCR enhancer, and cell lysis buffer.

The RT-PCR detection kit according to the present application, wherein the PCR enhancer is one or more of DMSO (dimethyl sulfoxide), Betaine, tetramethylammonium chloride (TMAC), and Trehalose, the cell lysis buffer is the solution of 1% Nonidet P-40, 150 mM Tris-HCl and 50 mM NaCl.

The RT-PCR detection kit the present application, wherein the kit further comprises one or both of a positive control and a negative control.

One non-limited embodiment of the application provides a multiple fluorescent direct RT-PCR detection method for detecting coronavirus in a patient using the detection kit according to the present application, comprising:

simultaneously amplifying a SARS-CoV-2 ORF1ab gene fragment, a SARS-CoV-2 N gene fragment, and an internal reference gene, and subjecting amplified products to a multiple fluorescence quantitative PCR detection by one-step in vitro amplification of multiple fluorescent probes, and determining if the sample is infected by the SARS-CoV-2 virus.

The multiple fluorescent direct RT-PCR detection method according to the present application, comprising:

obtaining a PCR detection working solution by mixing a PCR reaction solution with a solution mixture of target gene primes and probes, and enzyme mixture with a Hot Start Taq polymerase and a reverse transcriptase in the detection kit;

using the extracted SARS-CoV-2 virus as a template, to transcribe a corresponding DNA by a reverse transcriptase at a temperature of 50° C., using the corresponding DNA as a template, to perform a PCR reaction in the PCR reaction solution with Hot Start Taq polymerase under set chain reaction conditions;

choosing FAM (IFV-A), HEX (IFV-B), ROX (ORF1ab/N), and Cy5 (internal reference housekeeping gene) for a multiple reaction simultaneous testing, different dyes used for probe labeling do not affect the actual effects of the kit.

setting the threshold, analyzed by computer to obtain a Ct value, and determining if the patient is infected by the SARS-CoV-2 virus.

The multiple fluorescent direct RT-PCR detection method according to the present application, wherein the final concentrations of a PCR reaction system in the PCR step are following:

the concentration of $Mg^{2+}$ in the PCR buffer is 1-3.5 mM, the concentration of dNTP is 0.1-0.5 mM, the concentration of the upstream primers, the downstream primers and the probe upstream and downstream primers of IFV-A, IFV-B, and SARS-CoV-2 specific genes is 0.1-1.0M, the concentration of the probes is 0.1-0.5M, the concentration of Hot Start Taq enzyme is 0.5-5 U/reaction, and each test comprises 5-1000 copies of viral genome template.

The multiple fluorescent direct RT-PCR detection method according to the present application, wherein PCR reaction conditions are as follows: 50° C. 10 min; 95° C. 30 sec; 5 cycles: 95° C. 5 sec, 55° C. 30 sec; 40 cycles: 95° C. 3 sec, and 60° C. 10 sec.

Using different primer and probe sequences can achieve the purpose of the present application, but the detection specificity and sensitivity need to be verified.

The detection sensitivity of the detection kit the present application can reach as low as 50 copies/ml, far exceeding the currently approved two-step novel coronavirus nucleic acid detection kit, and the fastest detection time is only within 40 minutes to complete the entire process of 96 clinical swab samples. This meets the recently requirement of the National Health Commission to complete the test within one hour.

The reagent and the detection kit of the present application have the following technical advantages:

(1) high sensitivity, using enhanced fluorescent probe quenching technology, using more preferred viral gene detection primers and probe sequences, with higher specificity and sensitivity, and the detection limit is as low as 5 copies per response to clinical samples;

(2) the detection speed is fast, the whole detection process is within 1 hour (40 minutes in high-speed amplification mode), virus-free nucleic acid extraction also supports high-speed amplification, compared with other similar commercial fluorescent PCR reagents, the time is reduced to ⅓ (the whole process of nucleic acid extraction and detection is about 2-4 hours for regular reagents);

(3) simple and safe operation, direct sample loading detection, simultaneous nucleic acid release and nucleic acid detection, realizing "sample in, result out" closed tube detection, effectively solving the problem of aerosol generation, reducing indoor pollution and personnel infection opportunities, and cooperate. The portable fluorescent PCR instrument is particularly suitable for on-site rapid diagnostic testing;

(4) synchronously distinguish between influenza and new coronavirus, prevent cross-infection, and improve the efficiency of classified diagnosis and treatment;

BRIEF DESCRIPTION OF THE DRAWINGS

FIG. 1 is a graph of PCR amplification curve of positive control by FluA/B and SARS-CoV-2 detection kit in accordance with at least one embodiment. Wherein ♦ line stands for SARS-CoV-2 gene, ■ line stands for FluA gene, ▲ line stands for FluB gene, and x line stands for internal control gene.

EXAMPLES

The following non-limiting examples may enable those of ordinary skill in the art to more fully understand the present application, but do not limit the present application. Any person familiar with the technical field in the technical scope disclosed in the present application, according to the technical solution of the present application and the inventive concept to make equivalent substitutions or changes shall belong to the protection category of the present application.

The Materials and Equipment Used are as Follows:

DNAZap™ (Ambion, cat. #AM9890) or equivalent.

RNAse Away™ (Fisher Scientific; cat. #21-236-21) or equivalent.

10% bleach (1:10 dilution of commercial 5.25-6.0% hypochlorite bleach).

96-well 0.2 mL PCR reaction plates (Applied Biosystems).

ABI 7500. Roche LightCycler480, Bio-Rad CFX96 and other real-time quantitative PCR instruments that meet the detection channel settings of the kit of the present application.

The materials used in the present application are commercially available.

Detection Methods

6-FAM, 6-carboxy-fluorescein.

HEX, 5-hexachloro-fluorescein

TAMRA, tetramethyl-6-carboxyrhodamine

ROX, 6-carboxy-x-rhodamine

Cy5, Indodicarbocyanine, the formula of Cy5 is

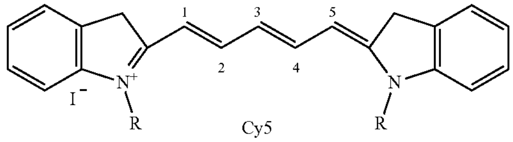

Cy5

BHQ-1 (Black Hole Quencher 1)

BHQ-2 (Black Hole Quencher 2)

Double-labeled fluorescent probes composed of the quenching group TAMRA, Eclipse or BHQ series dyes are often used as hydrolysis probes, or TaqMan probes, for real-time fluorescent quantitative PCR experiments.

1) TAMRA is a fluorescent dye that will fluoresce at a higher wavelength while quenching the reporter group. The Eclipse and BHQ series are non-fluorescent dyes. When the reporter group is quenched, the reporter group does not emit fluorescence. The probe fluorescence background is lower than that of TAMRA, and the detection sensitivity is higher.

2) The absorption spectrum of TAMRA covers a narrow range, and there are fewer types of reporter groups that can be matched with TAMRA; while Eclipse has a wider absorption range (390 nm-625 nm), and there are many types of reporter groups that can be quenched, such as FAM, HEX, TAMRA, ROX, etc. can be used; the combined use of BHQ series dyes has a wider range of absorption spectra, from 430 nm to near infrared, and there are more types of quenchable reporter groups, including Cy3, Cy5, etc. Therefore, a set of dual-labeled fluorescent probes can be composed of Eclipse or BHQ series dyes for multiple PCR.

HEX

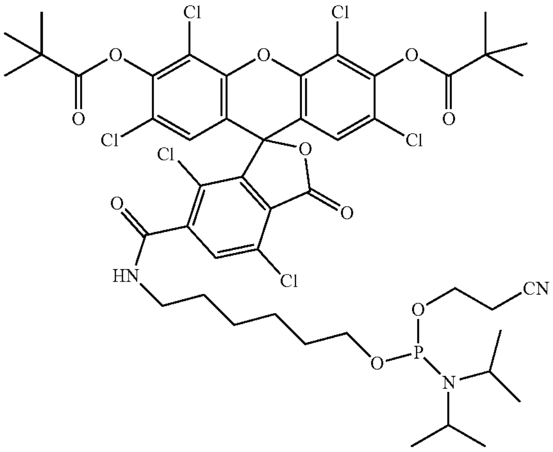

-continued

TET

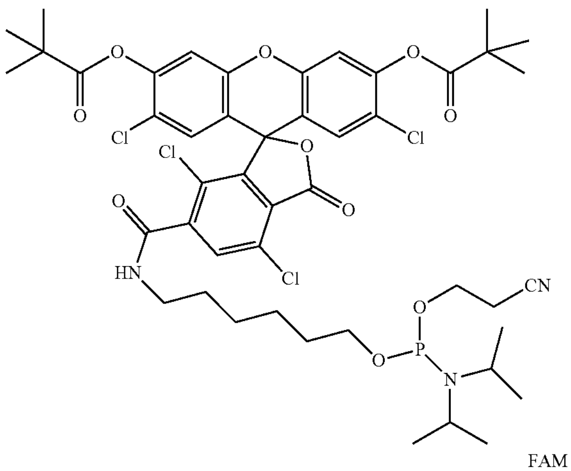

FAM

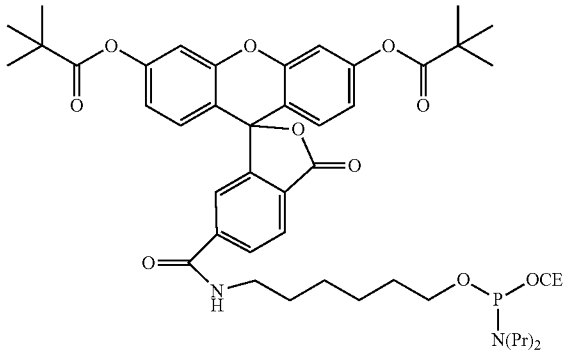

FAM, HEX and TET are added in the form of phosphite by B-cyanoethyl chemical action at the end of the synthesis cycle, so FAM, HEX and TET are added to the sugar at the 5' end of the primer instead of the base at the end of the primer. They are covalently linked to the last sugar ring at the 5'end through a phosphodiester bond.

Color in liquid: HEX is pink, FAM is yellow, TET is orange.

Oligonucleotides that have undergone these modifications of FAM, HEX and TET cannot undergo phosphorothioate modification.

Example 1. Kit Contents

TABLE 1

| Component | Specification | Description |
|---|---|---|
| 1. Reaction Mix | 900 μL/tube | Containing primer/probes for virus detection, PCR buffer, and 10 mM dNTP |
| 2. Enzyme Mix | 200 μL/tube | Mix of Hot Start Taq enzyme and reverse transcription enzyme |
| 3. Negative Ctrl (NC) | 200 μL/tube | Containing synthesis sequences of human actin gene |
| 4. Positive Ctrl (PC) | 200 μL/tube | Containing synthesis sequences of virus target gene fragments and IC |

*Composition and concentration of the active ingredient (s) of the reagent for Reaction mix by nature is 10 mM dNTP and 0.01 mM phosphate buffer solution, Enzyme mix is 0.5 U Hot Start Taq and reverse transcription enzyme, negative control is 0.1 μM dNTP and 0.01 mM distilled water, and positive control contains 0.2 μM dNTP and 0.01 mM distilled water. The device contains no other ingredients, which might influence the measurement.

Synthesis sequences of virus target gene fragments are primer sequences of a SARS-CoV-2 ORF1lab gene and primer sequences of a SARS-CoV-2 N gene.

Synthesis sequences of virus target gene fragments are sequence ID No. 1-2, 3-4, and IC is Sequence ID No. 13-14.

Example 2. Sample Collecting and Treatment

Sample Requirements

1. The test samples are clinical samples of novel coronavirus infections (nasal/pharyngeal swabs, sputum, lung lavage fluid/extracts, feces/anal swabs, etc.).
2. The kit of present application has a high tolerance to inhibitors, but excessive samples may cause inhibitors to exceed the tolerance of the reaction system, and excessive proteins and blood may coagulate at high temperature and block signal collection. To control the false negative caused by the inhibition of reaction, dilute the sample according to following "sample process".
3. The kit of present application cannot directly detect the samples collected by the inactivated sampling tube. Because the sample solution contains enzyme inactivator, this type of detection will fail. Such samples must be extracted and purified by nucleic acid before detection.

It is suggested that the samples with very low virus content should be tested after the virus is concentrated and the nucleic acid is extracted and purified. The kit of present application can be used for high-quality amplification with nucleic acid extract as its template.

For different types of samples, the treatment suggestions are as follows:

TABLE 2

| Samples types | Samples Collection and Proceed the Treatment |
|---|---|
| Nose/throat swab* | If collected by the virus sampling tube, after suspension, take 5 μL for detection |
| Deep expectoration, lung lavage/aspirate* | In case of collection by non-virus sampling tube, all samples shall be transferred into 3 ml virus sampling solution NS or PBS, distilled water, and the supernatant shall be taken off for sampling after being fully suspended (avoid floating objects), take 5 μL for detection |

TABLE 2-continued

| Samples types | Samples Collection and Proceed the Treatment |
|---|---|
| Anal swab | The samples collected by 3 ml virus sampling tube shall be directly processed after full suspension (anus swab samples containing a large amount of feces shall be treated as feces) |
| Feces | For the non-virus sampling tube, use a swab to take a proper amount (about the size of the swab head) and transfer the swab into 3 ml virus sampling solution or NS, PBS, distilled water. After fully suspending and centrifuging at 3000 rpm for 30 sec, take the supernatant for detection (avoid sediment) |
| Serum, Plasma | After 1:1 dilution and suspension with NS, PBS or distilled water |
| Whole blood (non heparin anticoagulation) | Dilute and suspend with NS or PBS solution 1:5, centrifuged at 3000 rpm for 30 sec, then take the supernatant and take 5 µL for detection |

The sample with * demonstrated the best results for the kit of the present application. When the specimen is not used for specific purposes such as culture, the specimen should be inactivated under 56° C. for 30 min and then proceed the treatment.

Example 3. System Preparation and Loading Sample

Melt the reagent thoroughly, and centrifuge the reagent to the bottom of the tube before use. The number of reaction tubes "n" corresponds to the number of samples and controls. Prepare a 25 µl reaction system according to the following method.

TABLE 3

| Reaction composition | Dosage |
|---|---|
| 1. Reaction Mix | 18 µL × number of specimens and controls (N) |
| 2. Enzyme Mix | 2 µL × number of specimens and controls (N) |

After system preparation for "n" samples, the total system solution for 20 µL/well should be added into 96 well plate separately, then 5 µL sample or positive control/negative control is added into each well. Finally, the centrifuge can be used to spin down the sample.

Example 4. Amplification

The kit of the present application employs the high-speed PCR with higher amplification efficiency and sensitivity (instrument support is required) and is compatible with conventional standard procedures for amplification.

TABLE 4

| High-speed amplification | Standard amplification | Detection channel |
|---|---|---|
| 50° C. 10 min;<br>95° C. 30 sec;<br>5 cycles:<br>95° C. 5 sec,<br>55° C. 30 sec<br>40 cycles:<br>95° C. 3 sec,<br>60° C. 10 sec<br>(read) | 50° C. 10 min;<br>95° C. 30 sec;<br>45 cycles:<br>95° C. 10 sec,<br>55° C. 30 sec<br>(read) | Flu-A: FAM,<br>520 nm<br>Flu-B: HEX/VIC,<br>555 nm<br>SAS-CoV-2:<br>ROX, 602 nm<br>IC: CY5, 668 nm |

Set the corresponding wavelength for the Roche machine. At lease, the reference fluorescence of the ABI machine and the quenching genes should both be set to 'None.'

Example 5. Quality Control

NC is not amplified, PC/IC is amplified, and Ct<30 indicates that the experiment is established. If these prerequisites are not met, the results will be invalid. The sample quality is acceptable as long as IC<30. If IC>30, resample and test again is necessary.

IC takes human housekeeper gene as the target (Cy5 as the detection channel), and effective samples (anal swab, pharyngeal swab, etc.) from human body should be positive. Using IC, investigation of the collection quality of human samples and whether there is excessive PCR inhibitor in the samples is possible. In the event of changes in the analytical performance of the device, when the positive control cannot be detected, the experiment should be retested or a new kit should be employed.

Example 6. Result Judgment

The typical "s" type amplification curve of the target gene of the sample shows that CT≤38 and CT value of IC (Cy5)<30, the target gene can be reported as positive. If the CT value>40, or if there is no amplification, the result can be reported as negative. However, if the CT value falls between 38 and 40, the results are unclear and should be reexamined. In this case, the process is re-conducted in some instances. At that point, the results can be interpreted as follows; and CT ≤38 is positive, and CT >38 is negative.

Example 7: Sensitivity Test

Performance Index of the Present Kit

LOD: the limitation of detection was 700, 500, 350, 500 copies/ml for FluA, FluB, SAS-CoV-2 and IC respectively.

The linear detection range is 500-$2\times10^7$ copies/ml.

LoD with Pseudo-Virus

The LoD of the Real-Time Fluorescent RT-PCR Kit for Detecting SARS-2019-nCoV was estimated by testing the standardized dilutions of pseudo-virus (n=3 each). The lowest target level at which all three replicates produced positive results was 100 copies/mL. This value was then confirmed by testing 20 replicates at five different concentrations above and below the estimated LoD (See Table 5).

TABLE 5

| LoD confirmation with pseudo-virus | | | | | | |
|---|---|---|---|---|---|---|
| N gene | | ORF1ab gene | | | | |
| Conc. (copies/ml) | Detection rate | Conc. (copies/ml) | Detection rate | Mean Ct N | Mean Ct ORF1ab | Mean Ct IC |
| 500 | 20/20 | 500 | 20/20 | 20.6 | 23.5 | 22.7 |
| 300 | 20/20 | 300 | 20/20 | 23.7 | 25.2 | 23.1 |
| 150 | 20/20 | 150 | 20/20 | 26.4 | 28.1 | 22.8 |
| 100 | 20/20 | 100 | 20/20 | 26.5 | 28.2 | 23.9 |
| 50 | 18/20 | 50 | 16/20 | 33.6 | 38.1 | 22.6 |

LoD with Clinical Specimens

The quantity of SARS-CoV-2 in three clinical specimens that were known to be positive was estimated by quantitative digital PCR. The remainder of each specimen was then diluted in SARS-CoV-2 negative clinical matrix to achieve the approximate concentrations shown in Table 6.

TABLE 6

| Dilution of clinical specimens for LoD determination | | | |
|---|---|---|---|
| | Dilution Factor | | |
| Concentration Estimated by Digital PCR (copies/mL) | Throat swab ($1.35 \times 10^4$ copies/mL) | BALF (broncho alveolar lavage fluid) 1 ($1.23 \times 10^4$ copies/mL) | BALF2 ($1.65 \times 10^4$ copies/mL) |
| 500 | 27 | 24.6 | 33 |
| 300 | 45 | 41 | 55 |
| 150 | 90 | 82 | 110 |
| 100 | 135 | 123 | 165 |
| 50 | 270 | 246 | 330 |

The LoD of the Real-Time Fluorescent RT-PCR Kit for Detecting SARS-2019-nCoV was evaluated by testing the dilutions of each clinical specimen described below (n=20 each). The LoD was determined to be the highest dilution at which ≥19/20 results were positive (i.e., ≥95% proportion positive) (See Table 7).

TABLE 7

| LoD confirmation | | | |
|---|---|---|---|
| Specimen | Concentration of SARS-CoV-2 estimated by Digital PCR (copies/mL) | Number Positive/ Number Tested | Proportion Positive |
| Throat swab | 500 | 20/20 | 100% |
| | 300 | 20/20 | 100% |
| | 150 | 20/20 | 100% |
| | 100 | 19/20 | 95% |
| | 50 | 17/20 | 85% |
| BALF1 | 500 | 20/20 | 100% |
| | 300 | 20/20 | 100% |
| | 150 | 20/20 | 100% |
| | 100 | 20/20 | 100% |
| | 50 | 17/20 | 85% |
| BALF2 | 500 | 20/20 | 100% |
| | 300 | 20/20 | 100% |
| | 150 | 20/20 | 100% |
| | 100 | 20/20 | 10% |
| | 50 | 16/20 | 80% |

Example 8: Specificity Test

The LoD (150 Copies/mL) for each clinical matrix was further validated for 3 lots of kits on a PCR system (Applied Biosystems™ Real Time PCR System 7500) in 20 replicates, where at least 19 tests confirmed positive for every matrix/kit.

a) Reactivity/Inclusivity:

Currently, different SARS-CoV-2 isolates are not available for the validation of reactivity/inclusivity of the kit. Primer/probe inclusivity was therefore evaluated by BLASTn analysis against 280 publicly available SARS-CoV-2 sequences on Mar. 10, 2020. Two Primes/probe set used in our kit exhibited 100% homology with all the available sequences. One set of primes/probe only exhibited 1 mismatch a single mismatch with one published sequence.

In addition to in silico analysis, 10 specimens from different regions of China confirmed as SARS-CoV-2 positive based on clinical criteria were used to validate the lower detection limit. The concentration of SARS-CoV-2 in each specimen was estimated with ddPCR. Further, each specimen was diluted to estimated concentrations of $5\times10^3$ Copies/mL and 100 Copies/mL (LoD concentration) and tested in replicates of 10 to evaluate the reproducibility of the test. The coefficient of Variation (CV) of Ct values at $5\times10^3$ copies/mL was lower than 5%. Table 8 below summarizes the results.

TABLE 8

| Concentration (Copies/mL) | | Testing results Reproducibility Diluted concentration (copies/mL) | Detection rate | CV | LoD Diluted concentration (copies/mL) | Detection rate |
|---|---|---|---|---|---|---|
| BALF1 | $1.23 \times 10^4$ | 1000 | 100% | 0.35% | 100 | 100% |
| BALF2 | $1.65 \times 10^4$ | 1000 | 100% | 0.46% | 100 | 100% |
| BALF3 | $1.55 \times 10^5$ | 1000 | 100% | 0.53% | 100 | 100% |
| BALF4 | $1.15 \times 10^4$ | 1000 | 100% | 0.72% | 100 | 100% |
| BALF5 | $5.35 \times 10^4$ | 1000 | 100% | 0.59% | 100 | 100% |
| BALF6 | $6.75 \times 10^4$ | 1000 | 100% | 0.86% | 100 | 100% |
| Throat swab 1 | $1.35 \times 10^4$ | 1000 | 100% | 1.24% | 100 | 100% |
| Throat swab 2 | $7.85 \times 10^4$ | 1000 | 100% | 0.47% | 100 | 100% |
| BALF7 | $1.75 \times 10^4$ | 1000 | 100% | 0.52% | 100 | 100% |
| BALF8 | $1.52 \times 10^4$ | 1000 | 100% | 0.74% | 100 | 100% |

Analytical Specificity:

The SARS-CoV-2 Real-time Reverse Transcriptase (RT)-PCR Kit utilizes identical oligo sequences, master mix, and amplification instruments.

A panel of more than 50 respiratory pathogens was tested with the SARS-CoV-2 direct-RT-PCR Kit of the present application, at clinically relevant concentrations (generally at 106 genome copies/mL). All pathogens were tested in triplicate and none produced any detectable reactivity with the SARS-CoV-2 direct-RT-PCR kit of the present application.

Specificity: No cross reaction with other coronaviruses or other viruses has been found, such as human coronavirus (hku1, OC43, n163 and 229E), SARS coronavirus and Mers coronavirus; H1N1 (new H1N1 influenza virus (2009), seasonal H1N1 influenza virus), H3N2, H5N1, H7N9, Victoria, respiratory syncytial virus A, B, parainfluenza virus 1, 2, 3, rhinovirus a, B, C, adenovirus 1, 2, 3, 4, 5, 7, 55, enterovirus a, B, C, D, human lung virus, human partial lung virus, EB virus, measles virus, human cytomegalovirus, rotavirus, norovirus, mumps virus, varicella zoster virus; also no cross reaction with bacterial cells as *Mycoplasma pneumoniae* and *Chlamydia* pneumonia.

Performance Index of the Present Kit

TABLE 9

Clinical results of Flu A/B and SARS-CoV-2 Direct RT-PCR kit of the present application compared with RT-PCR assay

| Target | RT-PCR assay | Direct RT-PCR Kit + | Direct RT-PCR Kit − | Sensitivity (%) | Specificity (%) | Accordance rate (%) | Kappa | P |
|---|---|---|---|---|---|---|---|---|
| Flu A | + | 236 | 1 | 99.57 | 100.00 | 99.81 | 0.975 | 6.524 |
| | − | 0 | 293 | | | | | |
| Flu B | + | 235 | 2 | 99.15 | 100.00 | 99.62 | 0.972 | 2.531 |
| | − | 0 | 293 | | | | | |
| SARS-CoV-2 | + | 236 | 1 | 99.58 | 99.44 | 99.43 | 0.968 | 3.451 |
| | − | 2 | 291 | | | | | |
| Conclusion | + | 707 | 4 | 99.72 | 99.54 | 99.62 | 0.975 | 2.610 |
| | − | 2 | 877 | | | | | |

Total 530 specimens were enrolled and tested in the study to evaluate the performance of the Flu A/B and SARS-CoV-2 Direct RT-PCR Kit of the present application in detecting Flu A/B and SARS-CoV-2 from of throat swab specimens, BALF, and extracted RNA obtained from Zhejiang Jiaxing Center for Disease Control of China compared to the clinical diagnosis of COVID-19 and results by National CDC kit of China, RT-PCR of Flu A, Flu B and SARS-CoV-2 showed overall positive and negative percent agreement across all specimens of 98.65%, 99.66% and 99.81% (95% CI: 97.8% to 99.9%) respectively. Wherein, the RT-PCR assay contains other primer for detecting Flu A, Flu B and SARS-CoV-2.

We claim:

1. A (RT)-PCR detection reagent system for detecting a coronavirus, comprising:

- a first plurality of primer sequences of a SARS-CoV-2 ORF1lab gene comprising:
  - a first upstream primer comprising the nucleotide sequence of SEQ ID NO. 1; and
  - a first downstream primer comprising the nucleotide sequence of SEQ ID NO. 2; and
- a second plurality of primer sequences of a SARS-CoV-2 N gene fragment comprising:
  - a second upstream primer comprising the nucleotide sequence of SEQ ID NO. 3; and
  - a second downstream primer comprising the nucleotide sequence of SEQ ID NO. 4;
- a third plurality of primer sequences of an influenza A (IFV-A) gene comprising:
  - a third upstream primer comprising the nucleotide sequence of SEQ ID NO. 5; and
  - a third downstream primer comprising the nucleotide sequence of SEQ ID NO. 6; and
- a fourth plurality of primer sequences of an influenza B (IFV-B) gene comprising:
  - a fourth upstream primer comprising the nucleotide sequence of SEQ ID NO. 7; and
  - a fourth downstream primer comprising the nucleotide sequence of SEQ ID NO. 8;
- a first fluorescent probe sequence of an influenza A (IFV-A) gene comprising the nucleotide sequence of SEQ ID NO. 9;

a second fluorescent probe sequence of an influenza B (IFV-B) gene comprising the nucleotide sequence of SEQ ID NO. 10;

a third fluorescent probe sequence of a SARS-CoV-2 ORF1lab gene comprising the nucleotide sequence of SEQ ID NO. 11;

a fourth fluorescent probe sequence of a SARS-CoV-2 N gene fragment comprising the nucleotide sequence of SEQ ID NO. 12; and an internal reference gene comprising:

a fifth upstream primer comprising the nucleotide sequence of SEQ ID NO. 13; and a fifth downstream primer comprising the nucleotide sequence of SEQ ID NO. 14.

2. The (RT)-PCR detection reagent system according to claim 1, further comprising:

a plurality of fluorescent probes comprising:

an IFV A-probe: FAM-SEQ ID NO. 16-BHQ1;

an IFV B-probe: HEX-SEQ ID NO. 17-BHQ1;

a first SAR-CoV-2-probe: ROX-SEQ ID NO. 18-BHQ2;

a second SAR-CoV-2 probe: ROX-SEQ ID NO. 19-BHQ; and an IC-probe: Cy5-SEQ ID NO. 20-BHQ2.

3. A multiple fluorescent direct (RT)-PCR detection method for detecting coronavirus in a patient using an (RT)-PCR detection reagent system consisting of upstream primers, downstream primers, and fluorescent probes, comprising:

obtaining a sample from the patient;

utilizing the detection regent system consisting of primers comprising SEQ ID NOS: 1-8 and primers comprising SEQ ID NOS: 13 and 14, a first IFV-A fluorescent probe comprising SEQ ID NO: 9, a second IFV-B fluorescent probe comprising SEQ ID NO: 10, a third SARS-CoV-2 ORF1lab gene fluorescent probe comprising SEQ ID NO: 11, and a fourth SARS-CoV-2 N gene fluorescent probe comprising SEQ ID NO: 12;

for simultaneous amplification of a SARS-CoV-2 ORF1ab gene fragment, a SARS-CoV-2 N gene fragment, and the internal reference gene of the sample to obtain amplified products without performing a nucleic acid extraction;

subjecting the amplified products to a multiple fluorescence quantitative PCR detection method comprising an in vitro amplification of multiple fluorescent probes; and detecting the presence of SARS-CoV-2 sequences in the patient sample.

4. A rapid multiple fluorescent direct (RT)-PCR detection method for detecting coronavirus in a patient using the (RT)-PCR detection reagent system of claim 3 comprising:

obtaining a sample from the patient;

initiating the (RT)-PCR detection method in a container using the detection reagent system for simultaneously amplifying the SARS-CoV-2 ORF1ab gene fragment, the SARS-CoV-2 N gene fragment, and the internal reference gene of the sample to obtain amplified products without performing an RNA extraction;

subjecting the amplified products to a multiple fluorescence quantitative PCR detection method in the container using an in vitro amplification of multiple fluorescent probes comprising SEQ ID NOS. 9-12, and wherein the multiple fluorescent probes further comprise:

an IFV A-probe: FAM-SEQ ID NO. 16-BHQ1;

an IFV B-probe: HEX-SEQ ID NO. 17-BHQ1;

a first SAR-CoV-2-probe: ROX-SEQ ID NO. 18-BHQ2;

a second SAR-CoV-2 probe: ROX-SEQ ID NO. 19-BHQ;

an internal reference probe: Cy5-SEQ ID NO. 20-BHQ2; and analyzing the results of the multiple fluorescence quantitative PCR detection method; and determining if the sample includes SARS-CoV-2 sequences, wherein the determination regarding the presence of SARS-CoV-2 sequences is completed with 60 minutes of obtaining the sample from the patient.

5. A rapid multiple fluorescent direct RT-PCR detection method according to claim 4, wherein the analyzing operation is conducted on point of care testing (POCT) quantitative PCR (qPCR) equipment.

* * * * *

SEQUENCE LISTING

```
<160> NUMBER OF SEQ ID NOS: 20

<210> SEQ ID NO 1
<211> LENGTH: 23
<212> TYPE: DNA
<213> ORGANISM: Artificial Sequence
<220> FEATURE:
<223> OTHER INFORMATION: Synthesized

<400> SEQUENCE: 1

ggtagtggag ttcctgttgt aga                                              23


<210> SEQ ID NO 2
<211> LENGTH: 24
<212> TYPE: DNA
<213> ORGANISM: Artificial Sequence
<220> FEATURE:
<223> OTHER INFORMATION: Synthesized

<400> SEQUENCE: 2
```

-continued aaggctttgt taagtcagtg tcaa 24

<210> SEQ ID NO 3
<211> LENGTH: 18
<212> TYPE: DNA
<213> ORGANISM: Artificial Sequence
<220> FEATURE:
<223> OTHER INFORMATION: Synthesized

<400> SEQUENCE: 3
gcgcttcagc gttcttcg 18

<210> SEQ ID NO 4
<211> LENGTH: 22
<212> TYPE: DNA
<213> ORGANISM: Artificial Sequence
<220> FEATURE:
<223> OTHER INFORMATION: Synthesized

<400> SEQUENCE: 4
gatggcacct gtgtaggtca ac 22

<210> SEQ ID NO 5
<211> LENGTH: 22
<212> TYPE: DNA
<213> ORGANISM: Artificial Sequence
<220> FEATURE:
<223> OTHER INFORMATION: Synthesized

<400> SEQUENCE: 5
gaccratcyt gtcacctctg ac 22

<210> SEQ ID NO 6
<211> LENGTH: 25
<212> TYPE: DNA
<213> ORGANISM: Artificial Sequence
<220> FEATURE:
<223> OTHER INFORMATION: Synthesized

<400> SEQUENCE: 6
gggcattytg gacaaakcgt ctacg 25

<210> SEQ ID NO 7
<211> LENGTH: 22
<212> TYPE: DNA
<213> ORGANISM: Artificial Sequence
<220> FEATURE:
<223> OTHER INFORMATION: Synthesized

<400> SEQUENCE: 7
tcctcaactc actcttcgag cg 22

<210> SEQ ID NO 8
<211> LENGTH: 21
<212> TYPE: DNA
<213> ORGANISM: Artificial Sequence
<220> FEATURE:
<223> OTHER INFORMATION: Synthesized

<400> SEQUENCE: 8
cggtgctctt gaccaaattg g 21

<210> SEQ ID NO 9
<211> LENGTH: 24
<212> TYPE: DNA

-continued

<213> ORGANISM: Artificial Sequence
<220> FEATURE:
<223> OTHER INFORMATION: Synthesized

<400> SEQUENCE: 9
tgcagtcctc gctcactggg cacg 24

<210> SEQ ID NO 10
<211> LENGTH: 27
<212> TYPE: DNA
<213> ORGANISM: Artificial Sequence
<220> FEATURE:
<223> OTHER INFORMATION: Synthesized

<400> SEQUENCE: 10
ccaattcgag cagctgaaac tgcggtg 27

<210> SEQ ID NO 11
<211> LENGTH: 27
<212> TYPE: DNA
<213> ORGANISM: Artificial Sequence
<220> FEATURE:
<223> OTHER INFORMATION: Synthesized

<400> SEQUENCE: 11
tgactctgca gttaaagccc tggtcaa 27

<210> SEQ ID NO 12
<211> LENGTH: 20
<212> TYPE: DNA
<213> ORGANISM: Artificial Sequence
<220> FEATURE:
<223> OTHER INFORMATION: Synthesized

<400> SEQUENCE: 12
ttgctgctgc ttgacagatt 20

<210> SEQ ID NO 13
<211> LENGTH: 21
<212> TYPE: DNA
<213> ORGANISM: Artificial Sequence
<220> FEATURE:
<223> OTHER INFORMATION: Synthesized

<400> SEQUENCE: 13
tgcccatcta cgaggggtat g 21

<210> SEQ ID NO 14
<211> LENGTH: 20
<212> TYPE: DNA
<213> ORGANISM: Artificial Sequence
<220> FEATURE:
<223> OTHER INFORMATION: Synthesized

<400> SEQUENCE: 14
ccgtggtggt gaagctgtag 20

<210> SEQ ID NO 15
<211> LENGTH: 23
<212> TYPE: DNA
<213> ORGANISM: Artificial Sequence
<220> FEATURE:
<223> OTHER INFORMATION: Synthesized

<400> SEQUENCE: 15
tcctgcgtct ggacctggct ggc 23

-continued

```
<210> SEQ ID NO 16
<211> LENGTH: 26
<212> TYPE: DNA
<213> ORGANISM: Artificial Sequence
<220> FEATURE:
<223> OTHER INFORMATION: Synthesized

<400> SEQUENCE: 16

tgcagtcctc gctcactggg cacgtc                                          26


<210> SEQ ID NO 17
<211> LENGTH: 29
<212> TYPE: DNA
<213> ORGANISM: Artificial Sequence
<220> FEATURE:
<223> OTHER INFORMATION: Synthesized

<400> SEQUENCE: 17

ccaattcgag cagctgaaac tgcggtgag                                       29


<210> SEQ ID NO 18
<211> LENGTH: 28
<212> TYPE: DNA
<213> ORGANISM: Artificial Sequence
<220> FEATURE:
<223> OTHER INFORMATION: Synthesized

<400> SEQUENCE: 18

tgactctgca gttaaagccc tggtcagc                                        28


<210> SEQ ID NO 19
<211> LENGTH: 27
<212> TYPE: DNA
<213> ORGANISM: Artificial Sequence
<220> FEATURE:
<223> OTHER INFORMATION: Synthesized

<400> SEQUENCE: 19

tcgcgcattg gcatggaagt cacatag                                         27


<210> SEQ ID NO 20
<211> LENGTH: 23
<212> TYPE: DNA
<213> ORGANISM: Artificial Sequence
<220> FEATURE:
<223> OTHER INFORMATION: Synthesized

<400> SEQUENCE: 20

tcctgcgtct ggacctggct ggc                                             23
```